United States Patent [19]
Krupin

[11] Patent Number: 5,454,796
[45] Date of Patent: Oct. 3, 1995

[54] DEVICE AND METHOD FOR CONTROLLING INTRAOCULAR FLUID PRESSURE

[75] Inventor: Theodore Krupin, Winnetka, Ill.

[73] Assignee: Hood Laboratories, Pembroke, Mass.

[21] Appl. No.: 29,001

[22] Filed: Mar. 10, 1993

Related U.S. Application Data

[63] Continuation-in-part of Ser. No. 669,193, Apr. 9, 1991, abandoned.

[51] Int. Cl.$^6$ ................................................. A61B 17/00
[52] U.S. Cl. .......................... 604/294; 604/9; 604/257; 604/289; 604/328
[58] Field of Search .................... 604/8–10, 93, 604/247, 257, 289, 290, 294, 327, 328

[56] References Cited

U.S. PATENT DOCUMENTS

| | | | |
|---|---|---|---|
| 3,788,372 | 1/1974 | Donowitz | 604/9 |
| 4,037,604 | 7/1977 | Newkirk | 604/9 |
| 4,457,757 | 7/1984 | Molteno | 604/294 |
| 4,604,087 | 8/1986 | Joseph | 604/294 |
| 4,750,901 | 6/1988 | Molteno | 604/294 |
| 4,826,478 | 5/1989 | Schocket | 604/294 |
| 4,886,488 | 12/1989 | White | 604/294 |
| 5,071,408 | 12/1991 | Ahmed | 604/9 |
| 5,171,213 | 12/1992 | Price, Jr. | 604/294 |
| 5,178,604 | 1/1993 | Baerveldt et al. | 604/294 |

Primary Examiner—Stephen C. Pellegrino
Assistant Examiner—Jeffrey A. Schmidt
Attorney, Agent, or Firm—Kane, Dalsimer, Sullivan, Kurucz, Levy, Eisele and Richard

[57] ABSTRACT

An implantable device used in treating glaucoma includes a movable plate shaped and sized to fit in a single quadrant of an eye to provide maximum surface area. A drainage tube is attached to the plate and has a distal end for insertion into the anterior chamber of the eye to drain fluid. A valve is disposed in the tube to control the fluid pressure within the eye and prevent hypotony. The plate is made of soft surgical grade polymeric material to prevent extrusion from the body.

7 Claims, 2 Drawing Sheets

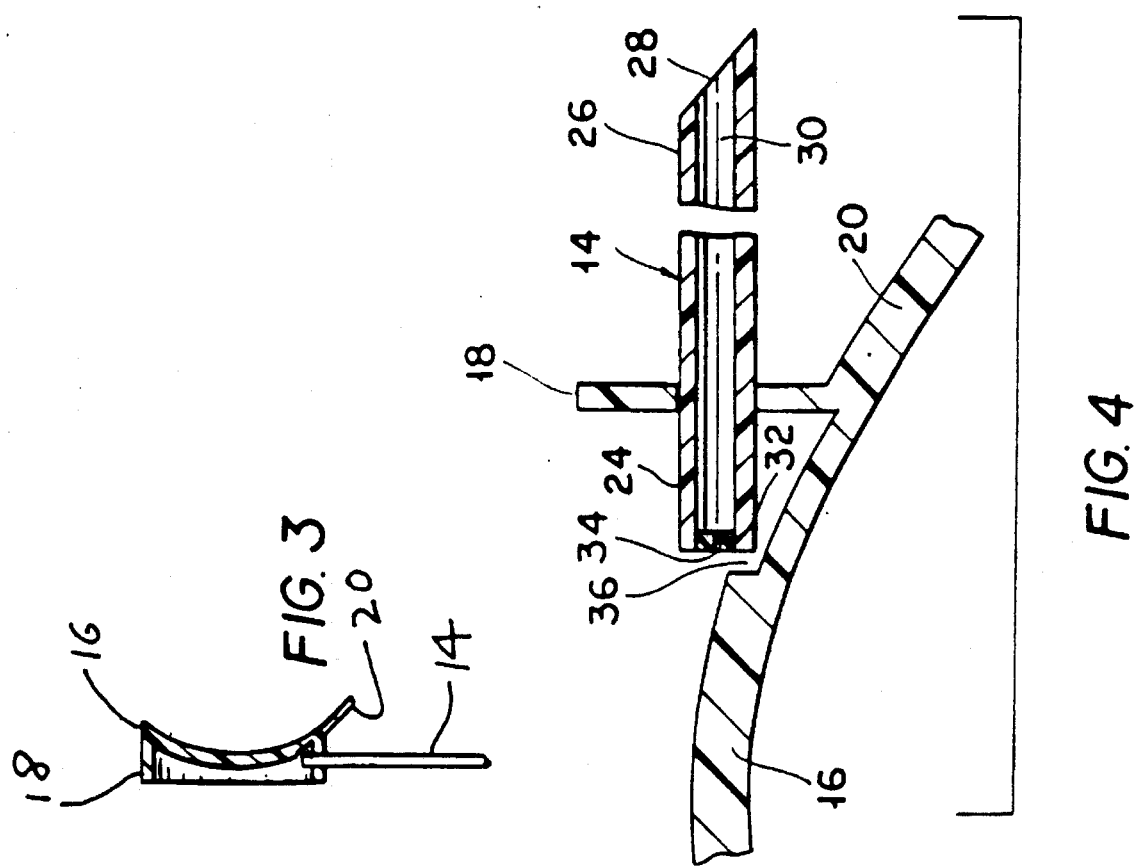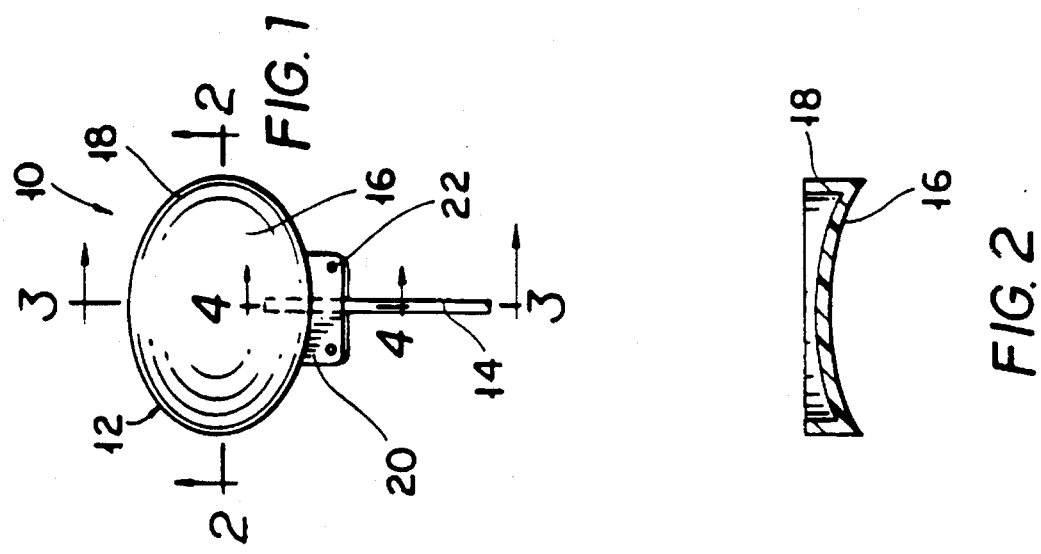

DEVICE AND METHOD FOR CONTROLLING INTRAOCULAR FLUID PRESSURE

CROSS-REFERENCE TO RELATED APPLICATION

This application is a Continuation-In-Part of my copending U.S. patent application Ser. No. 669,193 filed on Apr. 9, 1991 and now abandoned.

BACKGROUND OF THE INVENTION

1. Field of the Invention

This invention pertains to a device for use in the treatment of glaucoma, and more particularly to a drainage device implanted to lower the intraocular pressure of the eye by filtration.

2. Brief Description of Related Art

Glaucoma is a condition of the eye wherein the intraocular pressure is abnormally high. If this condition persists the optic nerve is damaged. It was discovered that glaucoma could be surgically treated by providing a drain to continuously withdraw excess aqueous humor fluid from the anterior chamber of the eye (glaucoma filtration surgery). Initially, this fluid was allowed to drain into the extraocular eye tissues; see for example U.S. Pat. No. 4,037,604. However, a problem with this approach was that over a period of time the surgical site was covered by fibrous scar tissue which occluded the drainage opening. In order to overcome this problem a band was proposed which covered the drainage hole to protect it from scar tissue; see *A Long Krupin-Denver Valve Implant Attached to a 180° Scleral Explant for Glaucoma Surgery*, Krupin et al. Ophthalmology Vol. 95, No. 9, September 1988, pp. 1174–1180.

In U.S. Pat. No. 4,457,757 to Molteno, instead of a band covering the drainage site a circular plate of uniform radius is used, having a convex face which faces away from the eye. The convex face of the plate receives a tube draining the anterior chamber of the eye. One or more additional round plates of uniform radius may be provided, which are coupled to the first plate and each other by secondary distribution tubes in a "daisy chain" fashion, because each plate individually may not have a sufficient capacity to hold a volume of drainage fluid sufficient to reduce intraocular pressure effectively. A problem with the multiple plate, daisy-chain structure is that it can drain the eye too fast, resulting in hypotony (a very low intraocular pressure) and a flattened anterior chamber. This condition makes further surgery more difficult and is disadvantageous to the patient since vision is impaired until normal pressure is restored (which may require several weeks). A further disadvantage is that the circular plates are fabricated of relatively hard material (i.e.; polypropylene) which must be solidly anchored in place on the eye sclera by four or more sutures spaced around the outer periphery of the plates.

In U.S. Pat. No. 4,750,901 (again to Molteno) an attempt was made to alleviate the problem of hypotony described above by placing a barrier or partition wall on the convex surface of the circular plate. Of course, this sub-dividing structure (to retard drainage) complicates fabrication and is difficult to mold. Moreover, multiple circular plates may still be required to insure a sufficient capacity for the drainage fluid.

In view of the above-mentioned disadvantages of the prior art, it is an objective of the present invention to provide a drainage device which consists of a single oval (elongate) plate having a capacity and surface area large enough to accommodate the drainage fluid, without encouraging hypotony.

Another objective is to provide a drainage device which is readily implanted and secured to the eye sclera by surgeons who have received minimum training and experience in similar implantations.

A further objective is to provide a drainage device with an integral and simple means of avoiding depressurizing the eye too fast.

Yet another objective is to provide a drainage device which is easy and economical to manufacture.

Other objectives and advantages of the invention shall become apparent from the following description of the invention.

SUMMARY OF THE INVENTION

The invention comprises a device for partial implantation in the anterior chamber of an eye for treating glaucoma, which comprises; an elongated (oval) plate sized and shaped to fit in a single quadrant (the area between two adjacent rectus muscles) on a recipient's eye; and an open tube connected at one end to the plate and having another end which is free so that it can be inserted into the anterior chamber of the eye. Advantageously, a valve is incorporated into the tube, preferably at the end connected to the plate, to provide a back-pressure for aqueous humor fluid. This permits the fluid from the eye to drain at a predetermined controlled rate. The drainage stops altogether if the eye pressure drops to a predetermined threshold level controlled by the valve. Preferably, the whole device is unitarily molded from a soft, surgical grade polymeric resin to facilitate attachment to the eye, trimming to fit and to avoid eye tissue erosion. The term "surgical grade" is used herein to mean that the resin is acceptable for implantation in a mammalian body. A preferred polymeric resin is silicone rubber.

BRIEF DESCRIPTION OF THE DRAWINGS

FIG. 1 shows a plan top of an embodiment device constructed in accordance with this invention;

FIG. 2 shows a side-sectional view of the device of FIG. 1 taken along line 2—2;

FIG. 3 shows a side sectional view of the device of FIG. 1 along line 3—3;

FIG. 4 shows an enlarged partial side-sectional view of the device of FIG. 1 taken along line 4—4.

DETAILED DESCRIPTION OF THE PREFERRED EMBODIMENTS OF THE INVENTION

Figure 5:
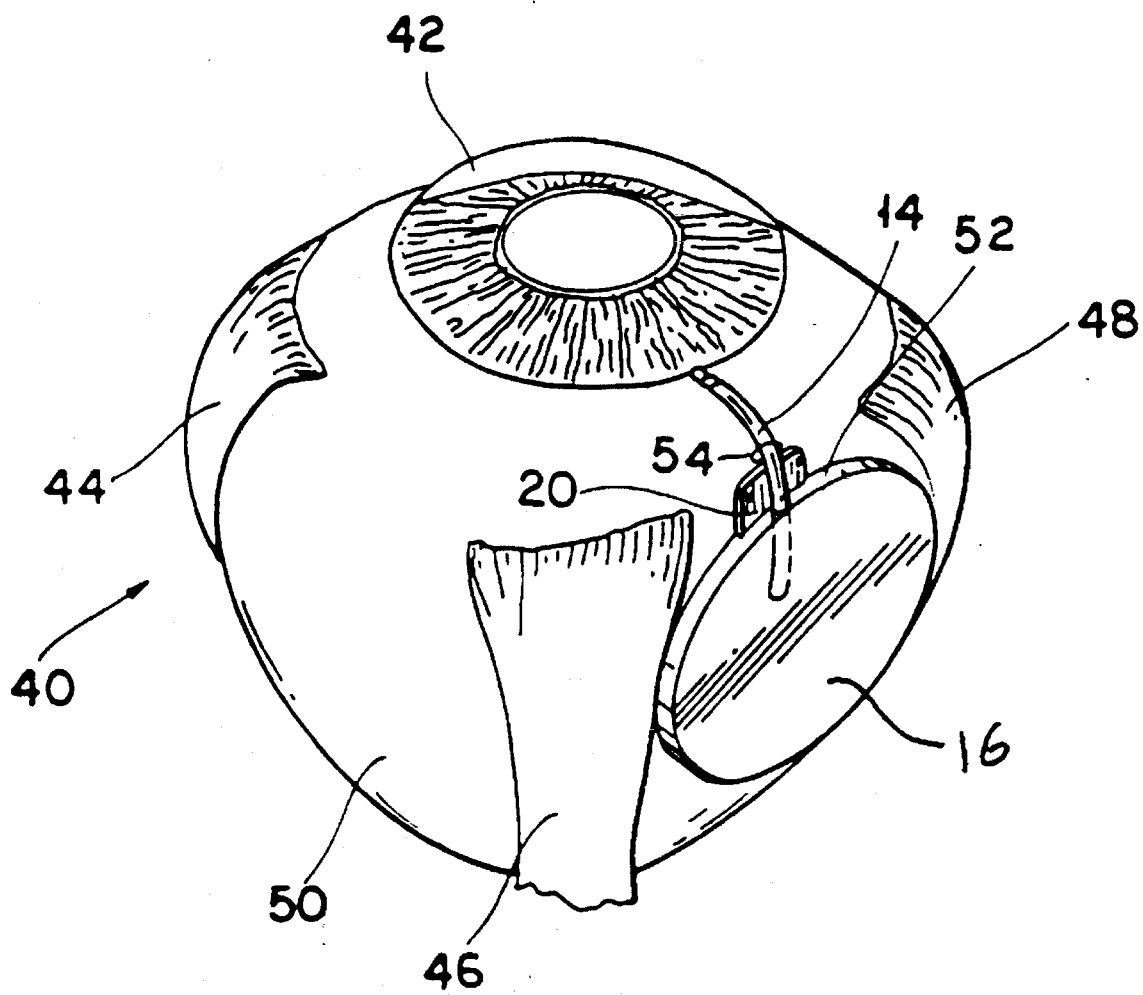
FIG. 5 shows an orthogonal view of an eye with an implanted device of FIG. 1.

Those skilled in the art will gain an appreciation of the preferred embodiments of the invention from a reading of the following description in conjunction with a viewing of the accompanying drawings of FIGS. 1–5, inclusive.

Referring now to the drawings, and more particularly FIGS. 1–4, a preferred device 10 constructed in accordance with this invention comprises an oval shaped plate 12 and an attached elongated tube 14. As shown more clearly in FIGS.

3 and 4, plate 12 comprises a bottom 16 having a concave lower surface for resting on the surface of an eyeball and a convex upper surface enclosed by an integral wall 18 on the periphery (circumference) of the bottom 16. Bottom 16 is curved so that when secured in place on an eye the lower concave surface will conform to and follow the curved outer surface of the eye. The upper convex surface may also be planar, but the convex configuration is preferred because it increases the area of the surface enclosed by wall 18. Importantly, as seen in FIG. 1, plate 12 is oval in outline when viewed from above, having for example a maximum length of about 18 mm and a maximum width of about 13 mm, i.e.; a radius differing from point to point around the periphery. Wall 18 may be about 2 mm high and advantageously is relatively thin, i.e.; having a thickness of from about 0.02 to 0.04 mm. Both bottom 16 and wall 18 may have a preferred thickness of about 0.03 mm, which is thinner than found on prior art devices. A thinner wall 18 enables the upper convex surface of bottom 16 to have a greater surface area. Preferably, plate 12 is made of surgical grade silicone rubber which is soft so that it will conform to and rest on the curved surface of the eye and will not be extruded by the patient's body. Representative is a softness of circa 45 Durometer (Shore A). This softness also permits folding of device 10 during handling to facilitate implant. Importantly, on one side occupying a minor portion of the plate periphery, the plate 12 is provided with an integrally molded suture wing or flange 20. Flange 20 may be provided with two holes 22 and functions as a means to suture the plate 12 to the eye. Two suture points at holes 22 facilitate suturing and reduce the surgeon's time and expertise needed for suturing. Having to suture to the eye anteriorly only is easier than suturing on posterior sites on the eyeball. As described above, a known prior art device is made of relatively hard polypropylene which requires implantation with four sutures spaced around the plate circumference to insure that the plate is not extruded by the eye as opposed to the present device which requires only one, preferably two sutures on one site off of the plate periphery, since the possibility of extrusion has been minimized. Also, since the flange 20 dictates the point of suturing to the eye, plate 12 is not held in constant and full contact with the underlying eye tissues but is hingedly held at a limited point or site. The softness of the device 10 permits the juncture between the bottom 16 and the flange 20 of plate 12 to function and flex as a hinge. This permits the bottom 16 to "float" freely on the underlying extraocular tissues and even to lift off the underlying extraocular tissues, while the flange 20 remains fixed and secured to the eye by one or two sutures. This occasional lifting and loss of contact with the underlying eye tissues is important to avoid erosion of the scleral tissues, reduce potential inflammation, potential infection and stimulation of tissue proliferation and scarring. When fixedly implanted, intraocular pressure may cause underlying tissue to lift and form a "bleb" over the plate. When the plate 12 is unable to move as described above, the total volumes of the bleb will increase, which may bring about inflammation and fibrosis.

At a preselected location, preferably immediately above flange 20, wall 18 is pierced through by tube 14. As shown in FIG. 4, tube 14 has a proximal end 24 which passes through wall 18 and a distal end 26 which is preferably angled as at 28 to facilitate its surgical insertion into the anterior eye chamber, and to avoid reducing the effective opening (diameter) of lumen 30. Location just above flange 20 serves to stabilize the tube 14 and anchor it against movement. End 24 may be terminated with a one-way fluid valve. The valve may be constructed for example by transversal slits 34 in an otherwise closed tube end as disclosed in U.S. Pat. No. 4,037,604, discussed above, and incorporated herein by reference. Only one slit 34 is shown in FIG. 4 for the sake of simplicity. Tube 14 may also be made of a soft surgical grade silicone rubber, preferably having an inner diameter of circa 0.012 mm. The durometer of the rubber may be selected to control elasticity of the valve lips and therefore the minimum pressure required to open the valve. Also, other factors affecting the pressure range of the valve operation include the length of the valve slits, thickness of the tube wall and like factors all of which are described in the aforementioned U.S. Pat. No. 4,037,604.

Preferably near end 24, bottom 16 on the convex surface is formed with a slight depression as at 36 to accommodate and receive the valve 32. This relatively low positioning of valve 32 protects it from the previously described bleb formation and premature clogging as was frequently observed in prior art devices. The higher profile of wall 18 also provides a means of supporting the bleb, enhancing fluid capacity of the device 10.

Referring now to FIG. 5, a typical eye ball 40 includes an anterior chamber 42. The eye is situated and moved by four rectus muscles 44, 46, 48 (the fourth rectus muscle is not visible in the Figure) disposed approximately equidistantly about the circumference of the eye. These four muscles define four quadrants about the eye, such as quadrants 50 and 52. As shown in FIG. 5, a device as described in FIGS. 1–4 is implanted by surgery so that plate 12 is nested in one quadrant, such as quadrant 52 on the surface of the eye between muscles 46 and 48. As previously mentioned, prior art devices comprised a circular plate. However, because of the way the muscles are arranged and connected to the eye, the size of such a circular plate of a single, given radius was limited to a radius of about 13.5 mm. As a result, a prior art single plate could not provide sufficient capacity and surface area to hold the fluid drained from the eye. Hence, several interconnected plates had to be used, as described above.

Advantageously, the single plate of the present invention has an elongate, oval shape. As a result, the plate can be placed between the muscles to provide a maximum area for external filtration. Attachment does not interfere with muscle functions. Tube 14 extends from the plate 12 across the surface of the eye into the anterior chamber 42. Tube 14, flange 20 and plate 12 are maintained in place by sutures as at 54. The plate 12, spaced from the site of suturing at flange 20 is free to move in and out of contact with underlying eye surface and is not fixed in position. The anterior site on the eye for suturing facilitates this procedure, even for less experienced surgeons, since the site is more accessible than posterior sites.

Numerous modifications may be made to the invention without departing from its spirit and scope as defined in the appended claims.

I claim:

1. An implantable soft silicone rubber device for draining a fluid out of an eye, consisting of;

a single oval plate having a bottom and a continuous sidewall surrounding said bottom said plate being of a size and shape to nest on the eye surface between adjacent rectus muscles of said eye;

a tube having a first end piercing said sidewall and a second end for insertion into the anterior chamber of said eye to drain a fluid therefrom;

a check valve disposed in said tube for controlling the pressure in said eye during drainage; and a flange hingedly attached to said plate for securing said plate to the surface of said eye, whereby the secured plate can move on the hinge to lift off underlying eye tissues.

2. The device of claim 1 wherein said valve is disposed at said first end.

3. The device of claim 1 wherein said bottom has a curvature matching the curvature of the eye.

4. An implantable, device for draining aqueous humor from the anterior chamber of an eye, which comprises;
   A. a single oval plate having
      (i) a concave lower surface for mating with and resting upon the curved surface of said eye;
      (ii) a convex upper surface for receiving the drained aqueous humor;
      (iii) a peripheral edge defining the outer boundary of the oval plate;
      (iv) a continuous sidewall on the peripheral edge, enclosing the upper surface; and
      (v) an aperture in the sidewall for receiving one end of a drainage tube described below;
   B. an elongate drainage tube having
      (i) a first end attached to the plate, received through said aperture and opening on the convex upper surface;
      (ii) a second open end free for surgical implantation into the anterior chamber of said eye; and
      (iii) an open lumen communicating between the first and second ends;
   C. check valve means disposed in the drainage tube; for controlling the flow of aqueous humor through the tube lumen; and
   D. flange means hingedly attached to a minor portion of the plate peripheral edge, for attaching said plate to the eye, such that the plate is hingedly free to lift off to a first position and return to a second position resting on the underlying eye surface tissue;
   said device being fabricated from a surgical grade of a synthetic polymeric resin.

5. The device of claim 4 wherein the convex upper surface includes a depression beneath the aperture, for receiving the first end of the tube, said check valve means being positioned on the first end of the tube.

6. A method of treating glaucoma which comprises;
   providing a device which comprises;
   A. a single oval plate having
      (i) a concave lower surface for mating with and resting upon the curved surface of said eye;
      (ii) a convex upper surface for receiving the drained aqueous humor;
      (iii) a peripheral edge defining the outer boundary of the oval plate;
      (iv) a continuous sidewall on the peripheral edge, enclosing the upper surface; and
      (v) an aperture in the sidewall for receiving one end of a drainage tube described below;
   B. an elongate drainage tube having
      (i) a first end attached to the plate, received through said aperture and opening on the convex upper surface;
      (ii) a second open end free for surgical implantation into the anterior chamber of said eye; and
      (iii) an open lumen communicating between the first and second ends;
   C. means disposed in the drainage tube; for controlling the flow of aqueous humor through the tube lumen; and
   D. flange means hingedly attached to a minor portion of the plate peripheral edge, for attaching said plate to the eye, the plate is hingedly free to lift off to a first position and return to a second position resting on the underlying eye surface tissue; said device being fabricated from a surgical grade of a synthetic polymeric resin; installing said device on the eye with said oval plate movably disposed between adjacent rectus muscles of the eye and said distal end disposed in the anterior chamber of the eye; and
   draining aqueous humor from said chamber, through the tube and onto the convex surface of the plate.

7. The method of claim 6 wherein installing includes folding the plate for ease of insertion on the eye.

* * * * *